(12) United States Patent
Nguyen

(10) Patent No.: US 6,534,003 B1
(45) Date of Patent: Mar. 18, 2003

(54) VALVE AND A METHOD OF USING A VALVE

(75) Inventor: Nick N. Nguyen, Costa Mesa, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/285,503

(22) Filed: Apr. 2, 1999

(51) Int. Cl.[7] .............................. A61L 2/00; A61L 9/00; A01N 1/00; F17D 3/00; F16K 7/00

(52) U.S. Cl. .............................. 422/33; 422/22; 422/28; 137/599.01; 137/599.07; 137/601.13; 137/601.14

(58) Field of Search .............................. 422/22, 23, 28, 422/33, 295; 137/599.01, 599.07, 601.13, 601.14

(56) References Cited

U.S. PATENT DOCUMENTS

| | | | | |
|---|---|---|---|---|
| 3,187,772 A | * | 6/1965 | Hanson, Jr. .................. | 137/599 |
| 3,951,184 A | * | 4/1976 | Rechtsteiner et al. .......... | 141/1 |
| 4,609,011 A | * | 9/1986 | Uehara ....................... | 137/601 |
| 4,989,637 A | * | 2/1991 | Dittrich ...................... | 137/599 |
| 5,289,811 A | * | 3/1994 | Covert et al. ................ | 137/599 |
| 5,413,759 A | * | 5/1995 | Campbell et al. ............. | 422/23 |

* cited by examiner

Primary Examiner—Robert J. Warden, Sr.
Assistant Examiner—Imad Soubra
(74) Attorney, Agent, or Firm—Blakely Sokoloff Taylor & Zafman (57) ABSTRACT

A valve is provided which includes a valve body, a first valve member, and a second valve member. The valve body has a first flow passage formed therethrough and a second flow passage formed therein. The second flow passage has a smaller cross-sectional area than the first flow passage so that the valve can be used interchangeable between systems requiring different flow rates through the valve, and so that flow through the valve can be more accurately controlled than through the first flow passage alone.

14 Claims, 4 Drawing Sheets

VALVE AND A METHOD OF USING A VALVE

BACKGROUND OF THE INVENTION

1). Field of the Invention

This invention relates to a valve, a method of operating a valve, and a method of operating a sterilization unit.

2). Discussion of Related Art

Sterilization units are commonly used for sterilizing objects such as surgical and other medical equipment. A sterilization unit of this kind which is commonly used includes a sterilization chamber into which objects such as surgical and other medical equipment are located. The pressure within the sterilization chamber is then reduced by pumping air out of the sterilization chamber through a valve which is located in line between the sterilization chamber and a pump. The valve controls the flow of the air to the pump. Once the pressure within the sterilization chamber is suitably reduced, a valve member within the valve is alternatingly opened and closed, or "throttled", to maintain the pressure within the sterilization chamber within relatively tight parameters.

The valve has a flow passage therethrough with a cross-sectional area which is optimally chosen both for quick discharge of air from the sterilization chamber and for accurately controlling the pressure within the sterilization chamber by throttling. The valve also has inlet and outlet openings which are chosen so as to match an outlet from the sterilization chamber and an inlet into the pump, respectively.

Sterilization units differ from one another because they have smaller or larger sterilization chambers and pumps, depending on requirement. Sterilization chambers of different sterilization units typically have 72 liter, 170 liter, or 270 liter internal volumes. The flow rates required to quickly reduce pressures or more accurately control pressures within the respective chambers therefore differ from one another. A different size valve and pump are therefore required on each of the different size sterilization chambers. Ideally, one design valve should, at least in part, be usable on sterilization chambers having different internal volumes while still allowing both for quick discharge of air or other fluids from, and for accurate control of pressures, of different size sterilization chambers by throttling. Ideally, the valve should be simple in design and should preferably not, for example, be a butterfly valve or a gate valve which is expensive to manufacture.

Some processes disclose using two valves for controlling pressure within a sterilization chamber, such as in U.S. Pat. No. 5,851,485 assigned to Johnson & Johnson Medical, Inc. of New Brunswick, N.J. which is for a system other than the system which is described herein.

SUMMARY OF THE INVENTION

According to one aspect of the invention a valve is provided which includes a valve body, a first valve member, and a second valve member. The valve body has a first flow passage formed therethrough and a second flow passage formed therein. The first flow passage has a first cross-sectional area and has first and second portions. The second flow passage has a second cross-sectional area which is smaller than the first cross-sectional area and has first and second sections. The first section has an end terminating in the first portion, and the second section has an end terminating in the second portion. The first valve member is mounted to the body for movement between substantially open and substantially closed positions. In the open position the first and second portions are in communication with one another to allow for flow of fluid into the first portion, from the first portion into the second portion, and from the second portion out of the valve body. In the closed position, the first valve member substantially closes off communication between the first and second portions. The second valve member is mounted to the body for movement, independently from the first valve member, between substantially unshut and substantially shut positions. In the unshut position the first and second sections are in communication with one another to allow for flow of fluid from the first portion into the first section, from the first section into the second section, and from the second section into the second portion. In the shut position, the second valve member substantially closes off communication between the first and second sections.

The body is preferably made of material which is resistant to attack by hydrogen peroxide.

The first flow passage may include an annular seat and the first valve member may be a first plug member. The first plug member may have a sealing surface which, when the first plug member is in the open position, is displaced from the annular seat and, when the first plug member is in its closed position, seals circumferentially with the annular seat.

The valve body may include a main portion and a cap secured to the main portion so that the main portion and the cap jointly define the second portion of the first flow passage. The cap may have a shaft opening formed therein. The valve may further include a shaft which extends through the shaft opening into the valve body, and the first plug member may be secured to the shaft inside the valve body.

The first portion may form an inlet opening into the valve body having a cross-sectional area of at least 490 mm$^2$, and the second portion may form an outlet opening out of the valve body having a cross-sectional area of at least 490 mm$^2$. The inlet opening may have a cross-sectional area of at least 1250 mm$^2$ and the outlet opening may have a cross-sectional area of at least 1250 mm$^2$. More specifically, the inlet opening may have a cross-sectional area of at least 1960 mm$^2$ and the outlet opening may have a cross-sectional area of at least 1960 mm$^2$.

The first cross-sectional area may be at least 490 mm$^2$ and the second cross-sectional area may be less than 28 mm$^2$, in which case the first cross-sectional area may be at least 1250 mm$^2$, or may be at least 1960 mm$^2$.

The first portion may form an inlet opening into the valve body and the second portion may form an outlet opening out of the valve body and the valve may further include an adapter having a flow aperture formed therethrough. The flow aperture may have an aperture inlet and an aperture outlet which is larger than the aperture inlet. The adapter may be secured to the valve body so that the aperture outlet is located adjacent the inlet opening into the valve body.

The aperture inlet may have a cross-sectional area of less than 630 mm$^2$.

The aperture outlet may have a cross-sectional area of at least 1250 mm$^2$, or even a cross-sectional area of at least 1960 mm$^2$.

The aperture inlet may have a cross-sectional area of less than 1260 mm$^2$, in which case the aperture outlet may have a cross-sectional area of at least 1960 mm$^2$.

The second flow passage may be formed by a first hole in the valve body, and a second hole which extends out of the first hole intermediate ends thereof, and the body may further have a plug aperture formed therein and extending into the first hole on a side thereof opposing and over the second hole. The second valve member may be a second plug member which, when in the shut position is located over an end of the second hole, and moves away from the end of the second hole into the plug aperture when moving from the shut position into the unshut position.

The first hole may extend out of an outer surface of the valve body. The valve may further include a plug which closes off an end of the first hole extending out of the valve body.

The invention also provides a method of operating a valve. A first valve member is moved between substantially closed and substantially open positions so as to control flow of a fluid through a first flow passage to a valve body of the valve. A second valve member is moved between substantially unshut and substantially shut positions so as to control flow of the fluid through a second flow passage in the valve body, the second flow passage interconnecting first and second portions of the first flow passage on opposing sides of the first valve member when in the closed position, and having a cross-sectional area which is smaller than a cross-sectional area of the first flow passage.

The valve may be located in line between a chamber and a pump. The first valve member may be moved into the open position so as to reduce the pressure within the chamber from a high pressure to a low pressure. Thereafter, the second valve member may be alternatingly moved between the unshut and shut positions to maintain the pressure within the chamber below the high pressure.

The chamber may have an internal volume of at least 50, at least 100 liters, or at least 200 liters. The first valve member may be in the closed position when the second valve member is alternatingly moved between the unshut and shut positions.

Alternatively, the chamber may have an internal volume of at least 800 liters.

The invention also provides a sterilization unit comprising of a sterilization chamber, an inlet valve, a pump, and an outlet valve. The sterilization chamber has an inlet and an outlet. The inlet valve opens and closes the inlet into the sterilization chamber. The outlet valve is located in line between the outlet of the sterilization chamber and the pump. The outlet valve includes a valve body, a first valve member, and a second valve member. The valve body has a first flow passage formed therethrough and second flow passage formed therein. The first flow has a first cross-sectional area and having a first and second portions. The second flow passage has a second cross-sectional area which is smaller than the first cross-sectional area and has first and second sections. The first section has an end terminating in the first portion, and the second section has an end terminating in the second portion. The first valve member is mounted to the body for movement between open and closed positions. In the open position, the first and second portions are in communication with one another to allow for flow of fluid from the sterilization chamber into the first portion, from the first portion into the second portion, and from the second portion to the pump. In the closed position, the first valve member substantially closes off communication between the first and second portions. The second valve member is mounted to the body for movement, independently of the first valve member between unshut and shut positions. In the unshut position the first and second sections are in communication with one another to allow for flow of fluid from the first portion into the first section, from the first section into the second section, and from the second section into the second portion. In the shut position, the second valve member substantially closes off communication between the first and second sections.

The first flow passage preferably includes an annular seat and the first valve member is preferably a first plug member having a sealing surface. which, when the first plug member is located in the open position, is spaced from the annular seat and, when the first plug member is in the closed position, seals circumferentially with the annular seat.

The valve body may include a main portion and a cap. The cap may have a shaft opening from therein and may be secured to the main portion so that the main portion and the cap jointly define the second portion of the first flow passage. The valve may further include a shaft which extends through the shaft opening into the valve body, wherein the first plug member is secured to the shaft inside the valve body.

The invention also provides a method of operating a sterilization unit comprising a sterilization chamber and at least one pump. A first valve member is moved from substantially a closed position to substantially an open position so as to allow flow of fluid through a first flow passage, formed through a valve body, to the at least one pump. The valve member is then moved from the substantially open position to the substantially closed position. A second valve member is then alternatingly moved between substantially unshut and substantially shut positions to control flow of fluid through a second flow passage through a valve body to the at least one pump. The second flow passage has a cross-sectional area which is smaller than a cross-sectional area of the first flow passage.

The valve body through which the first flow passage is formed may be the same valve body through which the second flow passage is formed.

When the valve member is alternating moved between the unshut and shut positions, the pressure within the chamber is preferably so maintained between 300 milliTorr and 1000 milliTorr.

BRIEF DESCRIPTION OF THE DRAWINGS

The invention is further described by way of examples with reference to the accompanying drawings wherein.

DETAILED DESCRIPTION OF THE INVENTION

Figure 1:
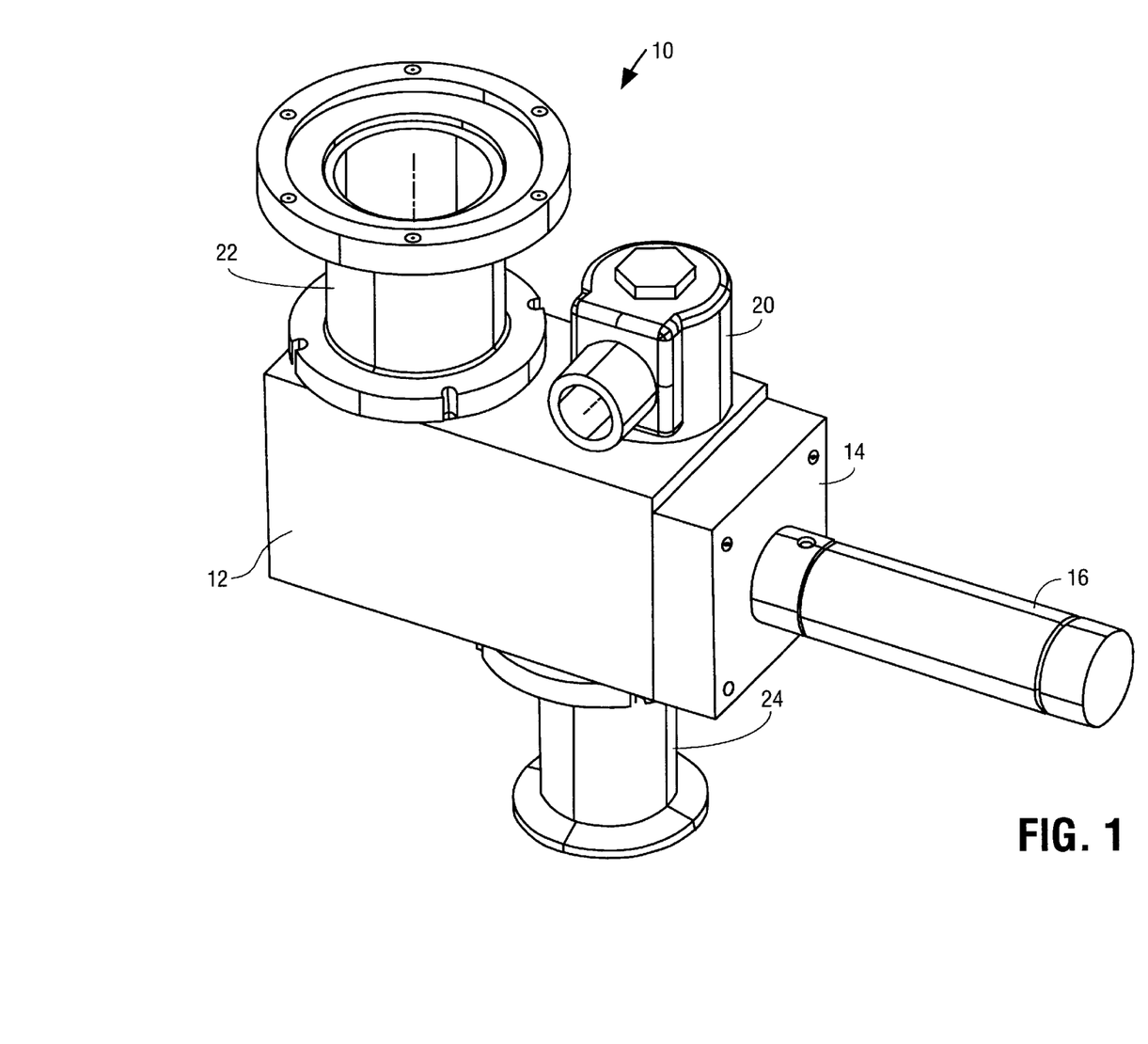
FIG. 1 is a perspective view of a valve according to an embodiment of the invention.
Figure 2:
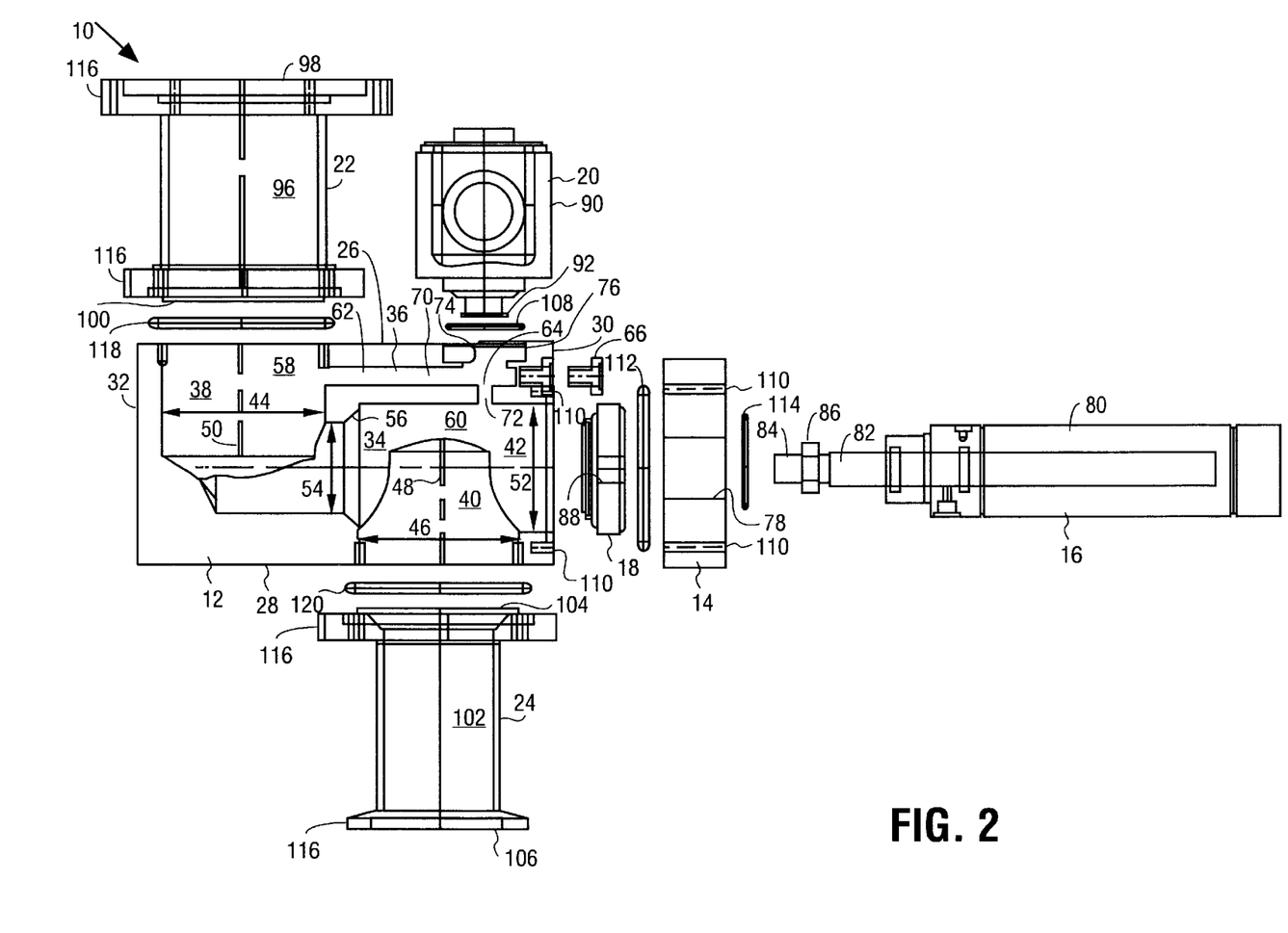
FIG. 2 is a cross-sectional side view of the valve before final assembly.

FIG. 1 of the accompanying drawings illustrates a valve 10 according to an embodiment of the invention. FIG. 2 illustrates the valve 10 before being fully assembled. The valve 10 includes a main body 12, a cap 14, a pneumatic cylinder 16, a first plug member 18, a solenoid assembly 20, an inlet adapter 22, and an outlet adapter 24.

The main body 12 is made out of a block of material with an upper surface 26 and a lower surface 28 opposing one another, and first and second end surfaces 30 and 32 opposing one another. First and second flow passages, 34 and 36, are formed respectively through and in the main body 12. The main body 12 may be made of any material which is resistant to attack from hydrogen peroxide, such as aluminum or steel, and is preferably made of aluminum for purposes of the ease of machinability.

The first flow passage 34 is formed by boring and inlet opening 38, an outlet opening 40, and the transverse opening 42 into the main body 12. The inlet opening 38 is formed into the upper surface 26 and has a diameter 44 of about 50 mm, and therefore a cross-sectional area of about 1963 mm$^2$. The outlet opening 40 is formed into the lower surface 28 and also has a diameter 46 of about 50 mm, and therefore a cross-sectional area of about 1963 mm$^2$. The outlet opening 40 has a center line 48 which is offset with respect to the center line 50 of the inlet opening. The inlet and outlet openings 38 and 40 are formed into the main body 12 to suitable depths so that portions of the inlet and outlet openings 38 and 40 are located next one another.

The transverse opening 42 is formed into the first end surface 30 and extends into the outlet opening 40 and from the outlet opening 40 through the main body 12 into the inlet opening 38. The transverse opening 42 is formed so as to have a larger diameter 52 through the outlet opening 40, and a smaller diameter 54 extending into the inlet opening 38. The smaller diameter 54 is about 28 mm so that the transverse opening 42 has a cross-sectional area of about 616 mm$^2$ in the region of the smaller diameter 54. The first flow passage 38 is also at its smallest in the region of the smaller diameter 54.

The annular seat 56 divides the first flow passage 34 into a first portion 58 and a second portion 60.

The second flow passage 36 is formed by drilling first and second holes, 62 and 64 respectively, into the main body 12. The first hole 62 is drilled into the first end surface 30, through the main body 12, into the first portion 58. An end of the first hole 62 extending out of the first end surface 30 is tapped to receive a self sealing screw 66. The second hole 64 is drilled into the upper surface 26 into the first hole 62 intermediate ends thereof and then out of the first hole 62 through the main body 12 into the second portion 60. It can thus be seen that the first and second holes 62 and 64 respectively form first and second sections 70 and 72 of the second flow passage 36. The second flow passage 36 has a diameter of about 5.4 mm throughout, and therefore a cross-sectional area of about 23 mm$^2$ throughout. The first section 70 has an end terminating in the first portion 58, and the second section 72 has an end terminating in the second portion 60. The second flow passage 36 thus has a smaller cross-sectional area than the first flow passage 34 and "bridges" the first flow passage 34, and in particular the annular seat 56.

A plug aperture 74 is also reamed into the upper surface 26 so that a portion of the second hole 64 extending from the upper surface 26 into the first hole 62 is removed. The plug aperture 74 extends into the first hole 62 on a side thereof opposing and over the remaining portion of the second hole 64. A portion of the plug aperture 74 near the upper surface 26 is then widened to form a solenoid body seat 76.

The cap 14 may be made of the same material has the main body 12. The cap 14 is in the form of a sheet metal member with a cylinder body opening 78 formed therein.

The pneumatic cylinder 16 is a conventional kind and is not described in detail herein. Suffice to say that the pneumatic cylinder 16 includes a cylinder body 80 and a shaft 82 mounted within and extending out of the cylinder body 80, and that the shaft 82 can be extended and retracted relative to the cylinder body 80 by correctly controlling flow of pressurized air into and out of the cylinder body 80. An end 84 of the shaft 82 is threaded and a nut 86 is located thereon.

The first plug member 18 is in the form of a circular disk with a shaft locating opening 88 formed therein. The first plug member 18 is preferably relatively resilient and is preferably made of a material which is resistant to attack by hydrogen peroxide, such as a material which is widely known as "Viton".

The solenoid assembly 20 includes a solenoid body 90 and a second plug member 92 secured to the solenoid body 90. The second plug member 92 can be extended from and retracted into the solenoid body 90 by operating a solenoid (not shown) located within the solenoid body 90. Further aspects of the solenoid assembly 20 are not described in detail herein as such aspects are conventional to solenoid assemblies in general.

The inlet adapter 22 has a flow aperture 96 formed therethrough which has an aperture inlet 98 and an aperture outlet 100. The aperture outlet 100 has a diameter and a cross-sectional area which is the same as that of the inlet opening 38. The aperture inlet 98 of the adapter 22 shown in FIG. 1 is about the same size as the aperture outlet 100. The aperture inlet 98 and the aperture outlet 100 therefore both have diameters of about 50 mm and cross-sectional areas of about 1963 mm$^2$. As will be further discussed herein, another adapter may be used wherein the aperture inlet 98 is smaller than the aperture outlet 100 so that the valve 10 may be used interchangeably within different systems as is intended by the design of the valve 10 itself.

The outlet adapter 24 also has a flow aperture 102 formed therein with an aperture inlet 104 and an aperture outlet 106. The aperture inlet 104 has a diameter and a cross-sectional area which is the same as that of the outlet opening 40. The aperture inlet 104 is thus about 50 mm in diameter and has a cross-sectional area of about 1963 mm$^2$. As shown in FIG. 1, the aperture outlet 106 is smaller than the aperture inlet 104. As will be further discussed herein, the aperture outlet 106 may differ from one outlet adapter to another to allow for interchangeable connection to different size pumps as the intended by the design of the valve 10 itself.

The components shown in FIG. 1 are all mounted, directly or indirectly, to the main body 12 as is now further described.

The solenoid assembly 20 is positioned so that the second plug member 92 is located within the plug aperture 74 and a portion of the solenoid body 90 is located within the solenoid body seat 76, and the solenoid body 90 is mounted to the main body 12 by means of bolts, screws or the like. A circular gasket 108 is located between the main body 12 and the solenoid body 90 so as to prevent leakage of fluid from the second flow passage 36 through an interface between the main body 12 and the solenoid body 90. The self sealing screw 66 is screwed into the end of the first hole 62. Once the solenoid assembly 20 and the self sealing screw 66 are in position, the second flow passage 36 is sealed off so as to be in communication only with the first flow passage 34.

The shaft 82 of the pneumatic cylinder 16 is inserted through the cylinder body opening 78 and a portion of the cylinder body 80 is located within the cylinder body opening 78, whereafter the cylinder body 18 is mounted to the cap 14 by means of bolts, screws or the like. The end 84 of the shaft 82 is then inserted into the shaft locating opening 88, and the first plug member 18 is then secured to the shaft 82 by locking the nut 86 onto the first plug member 18.

The cap 14 is then located against the main body 12 with the first plug member 18 located within the second portion 60. The cap 14 is then secured to the main body 12 by means of bolts, screws or the like which are inserted through holes 110 in the cap 14 and in the main body 12. The cap 14 finalizes the confines of the second portion 60 of the first flow passage 34. A circular O-ring seal 112 is located between the main body 12 and cap 14 to prevent leakage of fluid through an interface between the main body 12 and the cap 14. A gasket 114 is located between the cap 14 and the cylinder body 80 to prevent leakage of fluid through an interface between the cap 14 and the cylinder body 80.

Both the inlet and outlet adapters 22 and 24 include flanges 116 at ends thereof. The inlet adapter 22 is positioned with its aperture outlet 100 adjacent the inlet opening 38, and the inlet adapter 22 is secured to the main body 12 in a conventional manner by means of bolts, screws or the like which are inserted through holes (not shown) extending through the flange 116 at the outlet aperture 100, and into the main body 12. An O-ring seal 118 is located between the main body 12 and the flange 116 at the aperture outlet 100 and so as to prevent leakage of fluid through an interface between the main body 12 and the aperture outlet 22. The outlet adapter 24 is mounted to the main body 12 in a similar manner with its aperture inlet 104 located adjacent the outlet opening 40 and with an O-ring seal 120 located between the main body 12 and the flange 116 at the aperture inlet 104.

Figure 3:
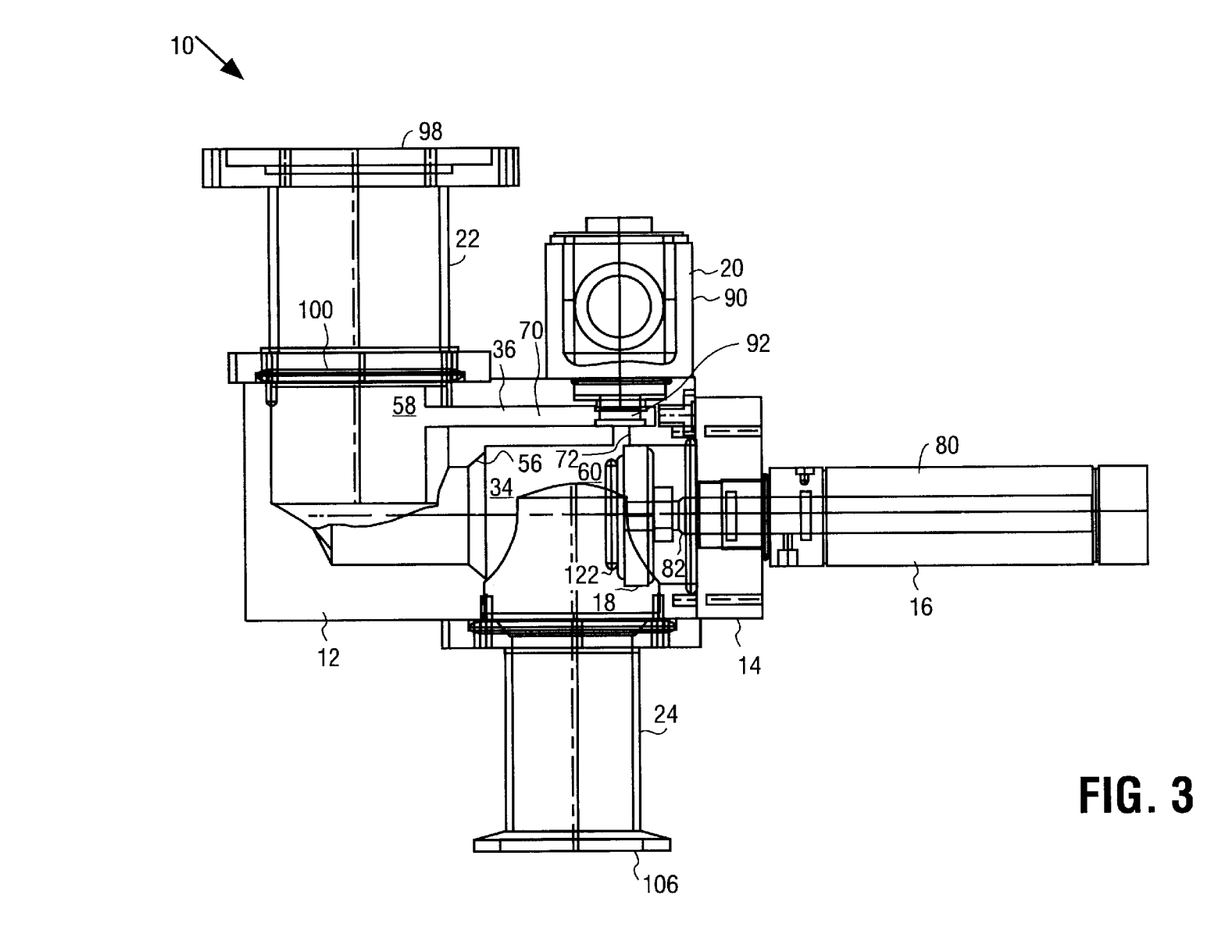
FIG. 3 is a view similar to FIG. 2 after the valve is assembled.

The FIG. 3 illustrates the valve 10 after being finally assembled as hereinbefore described.

By retracting the shaft 82 into the cylinder body 18, the first plug member 18 is moved away from the annular seat 56 into an "open" position wherein the first and second portions 58 and 60 are in communication with one another. A fluid is then allowed to flow into the inlet adapter 22, from the inlet adapter 22 into the first portion 58, from the first portion 58 into the second portion 60, and from the second portion 60 into the outlet adapter 24 and then out of the outlet adapter 24.

When the shaft 82 is extended from the cylinder body 80, the first plug member 18 is moved towards the annular seat 56 until a sealing surface 122 of the first plug member 18 is in contact with and seals with the annular seat 56. The first plug member 18 is then in a "closed" position wherein communication between the first and second portions 58 and 60 is substantially closed off. The fluid is then prevented from flowing through the first flow passage 34. The first plug member 18 can be moved between its open and closed positions by operating the pneumatic cylinder 16 so that the shaft 82 is extended or retracted relative to the cylinder body 80.

The second plug member 92 is movable independently from the first plug member 18. When the second plug member 92 is retracted into the solenoid body 90 it is moved into an "unshut" position. In the unshut position the first and second sections 70 and 72 are in communication with one another to allow for flow of fluid from the first portion 58 into the first section 70, from the first sections 70 into the second section 72, and from the second section 72 into the second portion 60. The fluid may so pass through the valve 10.

When the second plug member 92 is extended from the solenoid body 90 it is moved into a "shut" position. In the shut position, the second plug member 92 is located over an upper end of the second section 72. The second plug member 92 can be moved between its unshut and shut positions by operating the solenoid within the solenoid body 90.

The first flow passage 34 has a cross-sectional area which is much larger than that of the second flow passage 36. The first plug member 18 may be used for controlling the flow rates of large amounts of fluid through the valve 10. The second plug member 92 may, in turn, be used for accurately controlling the flow rates of small amounts of fluid through the valve 10. More importantly, the valve 10, excluding the inlet and outlet adapters 22 and 24, may be used interchangeably between a system requiring a large amount of fluid to pass through the valve 10, a system requiring a small amount of fluid to pass through the valve 10, a system requiring accurate control of large flow rates, or a system requiring accurate control of small flow rates.

For example, one system may require a small amount of fluid to pass through the valve 10. The first plug member 18 may be moved into its closed position, and the second plug member 92 may be used both for allowing fluid to pass through the valve 10, and for accurately controlling the fluid passing through the valve 10.

Another system may require an amount of fluid to pass through the valve 10 at a flow rate which may be too high for the small dimensions of the second flow passage 36 alone, but may still require control of flow of fluid through the valve 10 in a manner which would be more accurate than controlling the flow of the fluid through the valve 10 by means of the first plug member 18 alone. The first plug member 18 may be moved into its open position to allow for flow of fluid through the valve 10 which is less restricted than should the fluid flow through the second flow passage 36. The first plug member 18 may then be moved into its closed position and the second plug member 92 may be used for accurately controlling flow of smaller quantities of the fluid through the valve 10.

Yet another system may require an even larger amount of fluid to pass through the valve 10, and for flow of the fluid to be controlled at an accuracy which is commensurate with the flow rate of the fluid through the valve 10 generally. In such a system the first plug member 18 may be used both for allowing fluid to flow through the valve 10 and for accurately controlling flow of the fluid.

Figure 4:
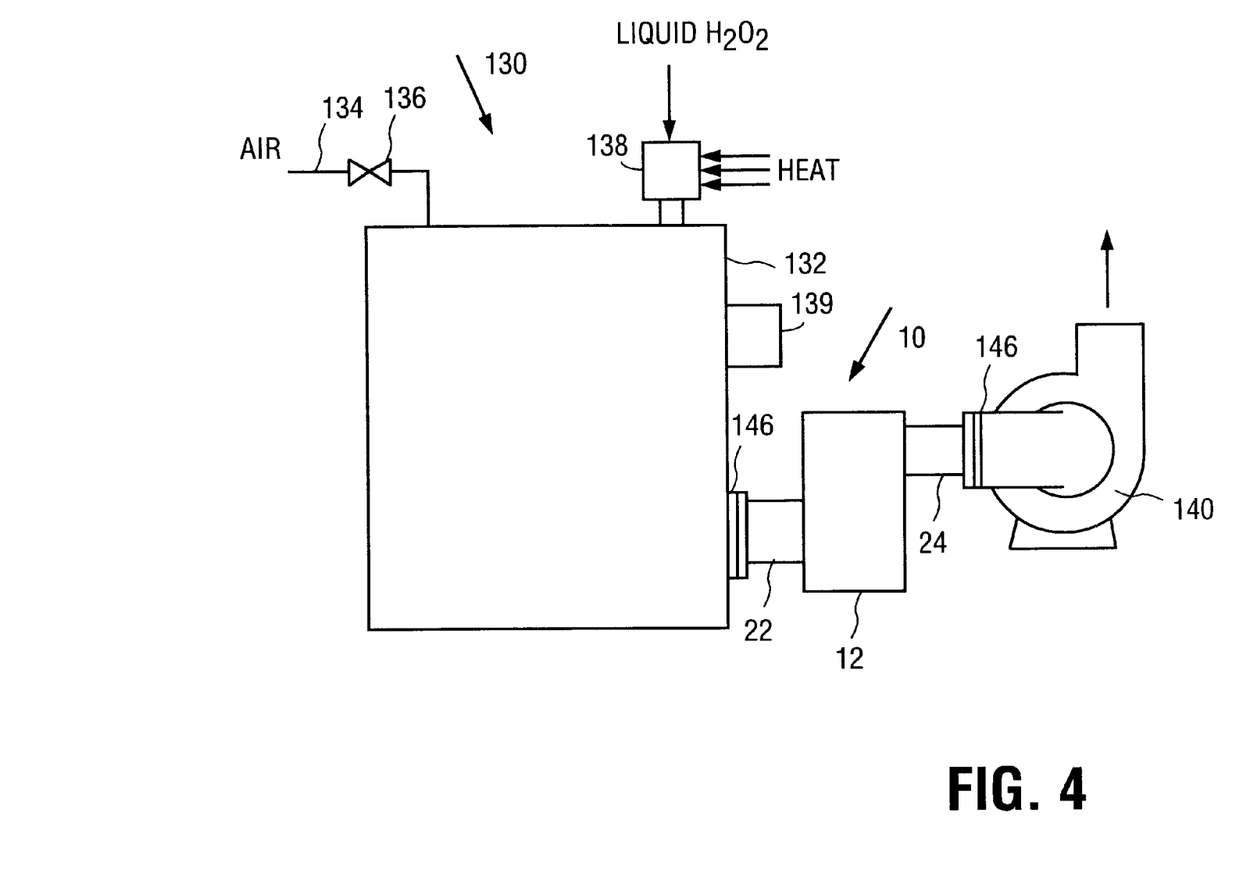
FIG. 4 is a side view illustrating one of many sterilization units wherein the valve finds particular application.

FIG. 4 illustrates a sterilization unit 130 wherein the valve 10 of FIGS. 1 to 3 finds particular application by acting as an outlet valve. In the discussion that follows regard should also be had to FIGS. 2 and 3 for a full understanding of how the sterilization unit 130 is operated. The sterilization unit 130 includes a sterilization chamber 132, an air inlet line 134 connected to an inlet of the sterilization chamber 132 through an air inlet valve 136, a hollow vaporizer 138 mounted to the sterilization chamber 132 and in communication therewith, a radio frequency (RF) plasma generator 139, a pump 140, and the valve 10 located in line between an outlet of the sterilization chamber 132 and the pump 140.

For purposes of illustration of an example of the invention, a system is described and discussed wherein the sterilization chamber 132 has a medium size internal volume of about 170 liters. The valve 10 has an inlet adapter 22 with an aperture inlet 98 having a diameter of about 25 mm, and an outlet adapter 24 with an aperture outlet 106 having a diameter of about 25 mm. The inlet adapter 22 and the outlet adapter 24 are selected so as to fit the dimensions of flanges 146 on the sterilization chamber 132 and the pump 140.

In use of the sterilization unit 130, objects such as surgical and other medical equipment which are to be sterilized are first located within the sterilization chamber 132. The pump 140 is then switched on. The pressure within the sterilization chamber 132 is then reduced from atmospheric pressure by closing the air valve 136 and opening the valve 10 so that air passes from the sterilization chamber 132 through the valve 10 to the pump 140. In order to quickly reduce the pressure within the sterilization chamber 132, with due consideration for its internal dimensions, the first plug member 18 is moved into its open position. The second plug member 92 may at this stage be in its unshut position or shut position. Once the pressure within the sterilization chamber 132 reaches about 800 mTorr (milliTorr), which typically occurs within about three minutes, the first plug member 18 is moved into its closed position.

In a first, preplasma stage, the plasma generator is then operated so as to create a radio frequency wave within the sterilization chamber 132. The radio frequency wave in the sterilization chamber 132 tends to cause evaporation of water and contaminants within the sterilization chamber 132 and in and an object located within the sterilization chamber 132. The pressure within the sterilization chamber 132 will tend to increase due to evaporation of water and contaminants located in and on the objects which are located within the sterilization chamber 132. The pressure within the sterilization chamber 132 is, however, controlled so as to remain within a relatively small band of between 600 and 1000 mTorr by alternatingly moving, or "throttling", the second plug member 92 between its unshut and shut positions for a sustained period of time of about 15 minutes. Due to the dimensions of the second flow passage 36 and the control which can be exercised over the second plug member 92, flow through the valve 10 and the pressure within the sterilization chamber 132 can be more accurately controlled to remain within the band of between 600 and 1000 mTorr with the second plug member 92 than with the first plug member 18 alone.

The second plug member is then moved into a shut position and the inlet valve 136 is opened so that air enters the sterilization chamber 132 until the pressure within the sterilization chamber 132 reaches atmospheric pressure. The inlet valve 136 is again closed and the first plug member 18 is moved into its open position, resulting in flow of air from the sterilization chamber 132 to the pump 140 and a quick reduction in pressure within the sterilization chamber 132 to a pressure of about 300 mTorr.

The first plug member 18 is then moved into its shut position, whereafter hydrogen peroxide is injected into the vaporizer 138. The vaporizer 138 is continuously heated so that the hydrogen peroxide immediately evaporates within the vaporizer 38 once injected. The vaporized hydrogen peroxide flows into the sterilization chamber 132, thus increasing the pressure within the sterilization chamber 132. Once the hydrogen peroxide is vaporized and diffused into the sterilization chamber 132, the air valve 136 is again opened to allow for flow of air into the sterilization chamber 132 until the pressure within the sterilization chamber reaches atmospheric pressure.

The pressure within the sterilization chamber may then again be reduced by opening the first plug member until the pressure within the sterilization chamber 132 reaches about 500 mTorr. The plasma generator 139 may then again be operated. In order to optimize the efficiency of a plasma generator 139, the pressure within the sterilization chamber 132 preferably has to be maintained within a relatively small band of between about 300 mTorr and 700 mTorr. For that purpose the second plug member 92 is again alternatingly moved between unshut and shut positions so as to maintain the pressure within the sterilization chamber 132 within such a relatively small band. Throttling may be continued for about 2 minutes, whereafter hydrogen peroxide may again be injected into the vaporizer 138 and the process will be repeated.

It should be understood that a central control unit (not shown) controls the air valve 136, injection of the hydrogen peroxide into the vaporizer 138, the solenoid of solenoid assembly 20, and the pneumatic cylinder. Details of the central control unit and other details of the sterilization unit are described in the specification of U.S. Pat. No. 5,656,238 which is assigned to Johnson & Johnson Medical, Inc. of New Brunswick, N.J. and which is hereby incorporated by reference.

As mentioned, the invention is described by way of example wherein the sterilization chamber 132 has an internal volume of 170 liters. The same valve 10, with other inlet and outlet adapters, may be used in a system having a sterilization chamber with a smaller internal volume of, for example, about 72 liters. In such a system an inlet adapter will typically be used having an aperture inlet with a diameter of about 10 mm, and an outlet adapter having an aperture outlet with a diameter of about 10 mm. In order to quickly reduce the pressure within the sterilization chamber of such a system, the first plug member 18 may be located in its open position and the second plug member 92 may be located in its shut or unshut position. The second plug member 92 may also be throttled at a lower pressure.

The same valve 10 may be used in another system having a much larger sterilization chamber of, for example, 270 liters or 1250 liters. In such a system an inlet adapter will typically be used having an aperture inlet of 50 mm, and an outlet adapter having an aperture outlet with a diameter of about 50 mm. In such a system the second plug member 92 may remain in its shut position at all times. The first plug member 18 may be used for reducing the pressure quickly within the sterilization chamber of such a system, and also be throttled to maintain a pressure of between 600 and 1000 mTorr.

Not only does the valve 10 make provision for quick discharge and accurate control of fluid flow interchangeably within systems requiring very low to very high flow rates, but the components and features of the valve 10 are intricately laid out in a compact, workable fashion. The manner in which the valve is constructed to open and close the first flow passage 34 is similar in design to a globe valve, which makes a valve relatively inexpensive to manufacture, especially when compared to a similar construction which is, for example, in the form of a butterfly valve or a gate valve.

While certain exemplary embodiments have been described and shown in the accompanying drawings, it is to be understood that such embodiments are merely illustrative and not restrictive of the current invention, and that this invention is not restricted to the specific constructions and arrangements shown and described, since modifications may occur to those ordinarily skilled in the art.

What is claimed:

1. A method of operating a sterilization unit comprising a sterilization chamber and at least one pump, the method comprising:

positioning a first valve member in substantially an open position so as to allow flow of a fluid from the chamber through a first flow passage formed through a valve body, to the at least one pump;

thereafter positioning the first valve member in substantially a closed position; and alternatingly moving a second valve member between substantially shut and substantially unshut positions, while the first valve member is in the substantially closed position, to control flow of the fluid from the chamber through a second flow passage formed through a valve body to the at least one pump, the second flow passage having a cross-sectional area which is smaller than a cross-sectional area of the first flow passage.

2. The method of claim 1 wherein the valve body through which the first flow passage is formed is the same valve body through which the second flow passage is formed.

3. The method of claim 2, wherein the first flow passage has a first cross-sectional area and first and second portions, and the second flow passage has a second cross-sectional area and first and second sections, the first section having an end terminating in the first portion, and the second section having an end terminating in the second portion.

4. The method of claim 3, wherein the valve body includes a main portion and a cap, having a shaft opening formed therein, and the cap is secured to the main portion so that the main portion and the cap jointly define the second portion of the first flow passage, the valve further comprising:

a shaft which extends through the shaft opening into the valve body, the first plug member being secured to the shaft inside the valve body.

5. The method of claim 1 wherein, when the second valve member is alternatingly moved between the shut and unshut positions, the pressure within the chamber is so maintained at between 300 milliTorr and 1000 milliTorr.

6. The method of claim 1 further comprising generating a plasma within the chamber.

7. The method of claim 1, wherein the first flow passage includes an annular seat and the first valve member is a first plug member have a sealing surface which, when the first plug member is positioned in the substantially open position, is spaced from the annular seat and, when the first plug member is in the substantially closed position, seals circumferentially with the annular seat.

8. The method of claim 1, wherein the fluid comprises hydrogen peroxide.

9. A method for operating a sterilization unit having a sterilization chamber, the method comprising:

reducing a pressure within the sterilization chamber to an operating pressure by evacuating contents of the sterilization chamber through a first opening having a first cross-sectional area;

closing the first opening; and maintaining the operating pressure to within defined limits by further evacuating contents of the sterilization chamber through a second opening by selectively opening and closing the second opening, the second opening having a cross-sectional area which is smaller than the first cross-sectional area.

10. The method of claim 9, wherein the first and second openings are each defined within a valve body of a valve.

11. The method of claim 10, wherein the first and second openings are defined within the same valve body.

12. The method of claim 11, wherein the operating pressure is between 600 and 1000 mTorr.

13. The method of claim 9, wherein the contents of the sterilization chamber comprises air.

14. The method of claim 13, wherein the contents of the sterilization chamber further comprise hydrogen peroxide.

* * * * *